United States Patent
Hartmann

[11] 3,950,381
[45] Apr. 13, 1976

[54] PREPARATION OF AROYL ACIDIC ESTERS
[75] Inventor: Peter Hartmann, Cologne, Germany
[73] Assignee: Bayer Aktiengesellschaft, Leverkusen, Germany
[22] Filed: Aug. 27, 1974
[21] Appl. No.: 501,016

[30] Foreign Application Priority Data
Aug. 31, 1973 Germany............................ 2343974

[52] U.S. Cl.......... 260/465 D; 260/469; 260/473 R; 260/476 R
[51] Int. Cl.$^2$.................. C07C 69/95; C07C 121/76
[58] Field of Search............. 260/476 R, 465 D, 469, 260/473 R

[56] References Cited
UNITED STATES PATENTS
2,407,942   9/1946   Wallingford et al................ 260/476

Primary Examiner—Lewis Gotts
Assistant Examiner—Dolph H. Torrence
Attorney, Agent, or Firm—Burgess, Dinklage & Sprung

[57] ABSTRACT

Aroyl acidic esters having the formula

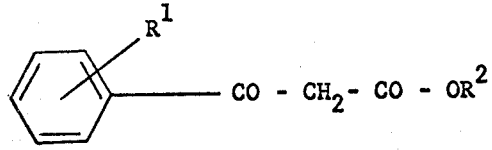

wherein
$R^1$ is hydrogen, $C_1$–$C_6$ alkyl, 5- or 6-membered cycloaliphatic, an aromatic radical with up to 12 C-atoms, $C_1$–$C_6$ alkoxy, aroxy with up to 12 C-atoms, halogen, cyano, or methyl or ethyl substituted by fluorine and/or chlorine; and
$R^2$ is $C_1$–$C_4$ alkyl,
are prepared by adding an arylmethyl ketone having the formula:

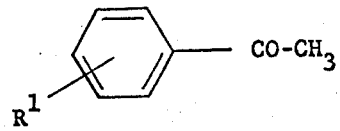

wherein $R^1$ is as defined above;
at a temperature in the range of from 50° to 140°C to excess dialkylcarbonate having the formula:

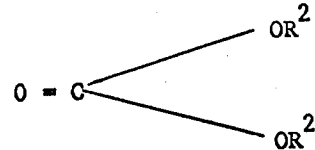

where $R^2$ is as defined above,
containing at least the stoichiometrically equivalent quantity of an alkali metal alcoholate based on the arylmethyl ketone, and simultaneously removing the alcohol liberated; and converting the alkali metal salt formed into the aroyl acetic ester by adding water and at least the stoichiometrically equivalent quantity of acid.

7 Claims, No Drawings

PREPARATION OF AROYL ACIDIC ESTERS

BACKGROUND

The invention relates to a process for the manufacture of aroyl acetic esters with almost quantitative yields.

The synthesis of some benzoyl acetic acid esters is already known (U.S. Pat. Nos. 2,407,942 and 2,367,632). However, the yields achieved are in the region of only 40 to 70%. The yields are low particularly when the phenyl nucleus is unsubstituted or is substituted by a substituent of the first order (G. Fodor, Organische Chemie, VEB Deutscher Verlag der Wissenschaften, Berlin, 1965, page 383).

SUMMARY

It has now been found that aroyl acetic esters can be obtained from excess carbonic acid dialkyl esters and arylmethyl ketones in the presence of an alkali metal alcoholate virtually free of by-products and in almost quantitative yields if an arylmethyl ketone with the formula (I):

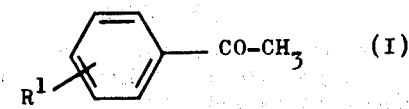

in which
R$^1$ represents hydrogen, a C$_1$–C$_6$ alkyl radical, a 5- or 6-membered cycloaliphatic radical, an aromatic radical with up to 12 C-atoms, a C$_1$–C$_6$ alkoxy radical, an aroxy radical with up to 12 C-atoms, halogen, cyano or a methyl or ethyl radical substituted by fluorine and/or chlorine, is added evenly over a period of more than 90 minutes at a temperature in the range of from 50° to 140°C to excess dialkyl carbonate with the general formula (II):

where
R$^2$ stands for an alkyl radical with 1 to 4 C-atoms, containing an alkali metal alcoholate in at least the stoichiometrically quantity relative to the arylmethyl ketone; and, at the same time, the alcohol released is distilled off, and the alkali metal salt formed is then converted into the aroyl acetic ester by adding water and at least the stoichiometrically quantity of acid; and the ester is then washed until neutral after isolation.

DESCRIPTION

Lower alkyl radicals are straight chain or branched alkyl radicals with up to 6 and preferably up to 4 C-atoms, for instance the isomeric hexyl and pentyl radicals, butyl, isobutyl, tertiary butyl, propyl and isopropyl. Methyl and ethyl are preferred.

The above-mentioned alkyl radicals are also suitable for the alkoxy radicals.

Apart from naphthyl and naphthoxy, phenyl and phenoxy are preferred as the aryl and aroxy radicals.

Of the halogens (fluorine, chlorine, bromine and iodine), fluorine and chlorine are preferred.

The arylmethyl ketones used for the process are known or are obtainable by known processes, for example according to Houben-Weyl, Methoden der org. Chemie, volume 7, parts 2a and 2b, Georg Thieme Verlag, Stutgart (1973), see especially pages 24, 29, 39, 40, 45, 49 and 63.

The following are examples for arylmethyl ketones: 4-acetylbiphenyl, p-chloracetophenone, p-cyanoacetophenone, o-methoxyacetophenone, p-methoxyacetophenone, p-phenoxyacetophenone, and p-trifluormethylacetophenone. Acetophenone is preferred.

Suitable alkyl radicals (R$^2$) apart from propyl, isopropyl, butyl, isobutyl and tertiary butyl, are preferably methyl and ethyl. The dialkyl carbonates used for the process are known or are obtainable by known processes, for example according to Houben-Weyl, Methoden der org. Chemie, volume 8, pages 105 to 107, Georg Thieme Verlag, Stuttgart (1952).

Suitable alcoholates are those of lower aliphatic alcohols of which ethanol and, in particular, methanol are preferred. Apart from potassium, sodium is also a preferred alkali metal. The quantity of alkali metal alcoholate used should be at least equivalent to the quantity of aryl methyl ketone, and it is preferable to work with a surplus of about 5 % by weight, but this can also be greater.

The reaction temperature is from 50° to 140°C, preferably in the range of from 60° to 85°C.

It is essential for the process according to this invention that an excess of arylmethyl ketone in the reaction mixture be avoided as far as possible. This is achieved in the invention by adding the ketone to the reaction mixture slowly and evenly so that, at any time, only a slight quantity of unreacted arylmethyl ketone is present in the reaction mixture.

However, it is also essential that only a slight quantity of the alcohol resulting from the reaction be present in the reaction mixture at any time, this quantity being kept as small as possible by simultaneous distillation. Ideally, the alcohol should be removed from the reaction mixture as it is formed. In practice, this is also achieved or promoted by the slow, even addition of the arylmethyl ketone. A corresponding design of the apparatus for the process can also be of assistance in this respect.

The process according to this invention can be used to particular advantage if the aromatic nucleus of the arylmethyl ketone is substituted by substituents of the first order (for example OCH$_3$) or is unsubstituted.

The reaction is generally carried out with the alcoholate corresponding to the dialkylcarbonate. However, it is preferred, irrespective of the dialkylcarbonate, initially to introduce the easily accessible sodium methylate in powder form with from 5 to 10 times the quantity of dialkylcarbonate, corresponding to the ketone used, and to distill off small proportions of alcohol via a column, optionally under a weak vacuum of from 100 to 500 torr. Thereafter, the ketone is continuously added over a period of more than 90 minutes and the alcohol formed is simultaneously distilled off, optionally under a weak vacuum of from 100 to 500 Torr, via a column.

In this context, continuous addition, apart from the strict meaning of the term, should also be understood to mean an addition in small quantities and at short time intervals, as obtained for example by dropwise addition or with hose pumps. It should be emphasised once more that even addition is aimed at keeping the quantities of arylmethyl ketone and released alcohol in the reaction mixture as small as possible.

If arylmethyl ketones that are solid at room temperature are used, it is best to add these in the form of a solution. The preferred solvent is the dialkylcarbonate used for the reaction. Naturally, other inert organic solvents can be used, as long as their boiling point is above that of the dialkylcarbonate. Examples of suitable solvents are toluene and xylene, or dioxan in the case of the dimethylcarbonate.

The reaction temperature is in the aforementioned range and is dependent on the carbonic acid ester used and on the reduced pressure applied. The addition time for the ketone is naturally somewhat dependent on the nature of the substituents present on the aryl radical, if any. It is generally in the range of from 1.5 hours to 12 hours, in particular from 2 to 8 hours, substituents of the first order (e.g., $OCH_3$) requiring longer reaction times than substituents of the second order (e.g., cyanogen) (G. Fodor, Organische, Chemie, VEB Deutscher Verlag der Wissenschaften, Berlin 1965, page 383), which need shorter addition times. After the surplus dialkylcarbonate has been distilled off, the alkali metal salts of the β-ketoester are obtained directly, and are than either immediately reacted further, or are converted into the free β-ketoesters in the usual way by acidifcation (aqueous HCl, aqueous $H_2SO_4$, acetic acid), the pH value being set at about 6. The esters are purified by crystallisation or distillation.

The aroyl acetic esters obtainable by the process according to this invention correspond to the formula (III):

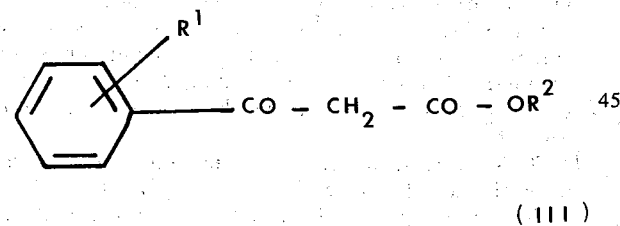

(III)

in which $R^1$ and $R^2$ are as defined above.

With the process according to this invention, a virtually quantitative conversion of the arylmethyl ketone used and a yield of corresponding pure aroylacetic ester of from 80 to 90% are obtained. These yields have not been obtainable hitherto by known processes.

The aroyl acetic esters than can be manufactured by this invention can be used for the synthesis of flavones (cf. Hans Beyer, Lehrbuch der Organischen Chemie, S. Hirzel Verlag Leipzig, P. 640 (1961)). Beilstein, Handbuch der Organischen Chemie, 4th Edition, Vol. 10, IIIrd Supplement, Springer Verlag Berlin, page 2991, (1972), gives further known uses of the esters produced by the process of the invention.

EXAMPLE 1

113 g of sodium ethylate are added to 800 cc diethylcarbonate and the mixture is distilled at 150 torr via a column (bath temperature 75° to 80°C). 250 g p-methoxyacetophenone dissolved in 200 cc diethylcarbonate are then added in even proportions over a period of 3.5 hours at 80°C, and the resulting alcohol is simultaneously fractionated off at 120 torr. The surplus diethylcarbonate is then removed by water jet vacuum, water is added to the remaining sodium salt and the solution is adjusted to pH 6 with acetic acid. The organic phase is separated off, the aqueous phase is extracted with 250 ml acetic acid ethyl ester, and the combined organic phases are then washed with water, dried and the solvent is removed. The residue is fractionated, 313 g (85% of the theoretical amount) of p-methoxybenzoyl acetic acid ester with a boiling point of 170° to 178°C/1.0 Torr being obtained.

The same result is achieved if, instead of the sodium ethylate, 90 g of sodium methylate are used.

EXAMPLE 2

The procedure is as described in Example 1, except that 54 g of sodium methylate in 600 ml dimethylcarbonate are used and 154.5 g of p-chloro-acetophenone are added dropwise over a period of 2.5 hours at 60°C. Working up in accordance with Example 1 gives at 60°C 187 g (87% of the theoretical amount) of p-chloro-benzoylacetic acid methyl ester with a boiling point of 113°C/0.3 torr.

The same result is achieved if the continuous addition of the p-chloro-acetophenone is carried out within about 90 minutes instead of within 2.5 hours.

EXAMPLE 3

189 g of sodium methylate are initially introduced into 1900 ml of diethylcarbonate, the mixture is distilled at 150 torr via a column (bath temperature 75° to 80°C), 420 g of acetophenone are then added in equal portions over a period of 2 hours and the resulting alcohol is simultaneously fractionated at 120 torr. Thereafter the surplus diethylcarbonate is removed under a water jet vacuum, water is added to the remaining sodium salt and the solution is adjusted to pH 6 with acetic acid. The organic phase is separated off, the aqueous phase is extracted with 500 ml acetic acid ethyl ester, and the combined organic phases are washed with water, dried and concentrated. The residue is distilled.

Benzoyl acetic acid ethyl ester is obtained in a yield of 87% of the theoretical amount, b.p. 115°–120°C/1.5 Torr.

Repetition of the experiment with an addition time of 2.5 hours gives a yield of 90% of the theoretical value. When the addition time is 5 hours, the yield is around 89% of the theoretical value.

EXAMPLE 4

250 g of sodium methylate are initially introduced into 3000 ml of dimethylcarbonate and the mixture is distilled via a column at 150 torr (bath temperature 75° to 80°C). A solution of 720 g of acetylbiphenyl (p-phenylacetophenone) in 1000 ml toluene heated to a temperature of 60° to 70°C is then added in equal proportions over a period of 2.5 hours at 75°C, and the resulting alcohol is fractionated off at 125 torr. Thereafter, the surplus dimethylcarbonate is run off at a further reduced pressure, warm water (50°C) is added to the remaining sodium salt suspended in toluene and the solution is adjusted to pH 6 with acetic acid. The organic phase is separated off, washed with water, dried and concentrated. The residue is then recrystallised from 3000 ml of cyclohexane. 883 g (87% of the theoretical amount) of p-phenylbenzoyl acetic acid methyl ester are obtained, melting point 82°C.

EXAMPLE 5

The procedure is as described in Example 1, except that 95 g of sodium methylate in 800 ml dimethylcarbonate are used and 250 g of o-methoxyacetophenone are added dropwise over a period of 5 hours at 90°C, the alcohol formed being simultaneously distilled off at normal pressure. Working up in accordance with Example 1 gives 100 g of unreacted starting material and 162 g of o-methoxybenzoylacetic acid methyl ester boiling at 130° to 133°C/0.07 torr (= 78% of the theoretical amount based on the reacted o-methoxyacetophenone).

EXAMPLE 6

Using Hershberg and Fieser's method, (Org.Syn.Coll. Vol. 2, 195 (1943), a suspension of potassium ethylate in ether is prepared from 20 g of potassium and the product is then concentrated to dryness by evaporation in vacuo. The potassium ethylate obtained is suspended in 250 cc of dry diethylcarbonate and the mixture is distilled at 150 torr via a column (bath temperature 75° to 80°C). A solution of 72.5 g of p-cyanoacetophenone in 150 cc of diethylcarbonate is then continuously added over a period of 2.5 hours at 80°C and the resulting alcohol is fractionated off at 120 torr. Working up in accordance with Example 1 gives 91 g (84% of the theoretical amount) of p-cyanobenzoyl acetic acid ethyl ester of b.p. 170° to 172°C/2.8 torr.

What is claimed is:

1. Process for preparing an aroyl acetic ester having the formula:

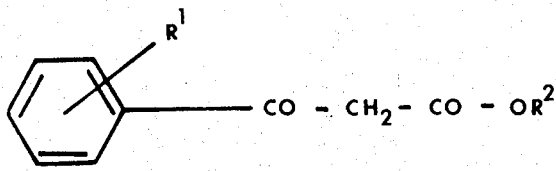

wherein
R$^1$ is hydrogen, C$_1$–C$_6$ alkyl, an aromatic radical with up to 12 C-atoms, C$_1$–C$_6$ alkoxy, aroxy with up to 12 C-atoms, halogen, cyano, or methyl or ethyl substituted by fluorine and/or chlorine; and
R$^2$ is C$_1$–C$_4$ alkyl,
which comprises adding an arylmethyl ketone having the formula:

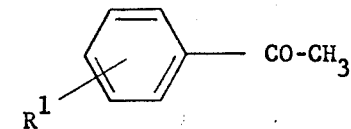

wherein R$^1$ is as defined above;
evenly over a period of at least 90 minutes at a temperature in the range of from 50° to 140°C to excess dialkylcarbonate having the formula:

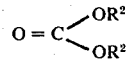

where R$^2$ is as defined above,
containing at least the stoichiometrically equivalent quantity of an alkali metal alcoholate based on the arylmethyl ketone, and simultaneously removing the alcohol liberated; and converting the alkali metal salt formed into the aroyl acetic ester by adding water and at least the stoichiometrically equivalent quantity of acid.

2. Process of claim 1 wherein the alcohol is removed by distillation.

3. Process of claim 1 wherein the ester is washed until neutral after isolation.

4. Process of claim 1 wherein the arylmethyl ketone is evenly added over a period of from 1.5 to 12 hours.

5. Process of claim 1 wherein a reduced pressure in the range of from 100 to 500 Torr. is applied.

6. Process of claim 1 wherein the arylmethyl ketone is solid at room temperature and is added in solution to the dialkylcarbonate.

7. Process of claim 1 wherein the alkali metal alcoholate used corresponds to the dialkylcarbonate.

* * * * *